(12) United States Patent
Götz et al.

(10) Patent No.: US 6,680,410 B2
(45) Date of Patent: Jan. 20, 2004

(54) METHOD FOR PRODUCING OXIME ETHERS

(75) Inventors: Roland Götz, Neulussheim (DE); Bernd Wolf, Fussgönheim (DE); Michael Rack, Heidelberg (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 0 days.

(21) Appl. No.: 10/257,327

(22) PCT Filed: Apr. 4, 2001

(86) PCT No.: PCT/EP01/03822
§ 371 (c)(1), (2), (4) Date: Oct. 10, 2002

(87) PCT Pub. No.: WO01/77070
PCT Pub. Date: Oct. 18, 2001

(65) Prior Publication Data
US 2003/0109740 A1 Jun. 12, 2003

(30) Foreign Application Priority Data
Apr. 11, 2000 (DE) .......................... 100 17 724

(51) Int. Cl.[7] ................. C07C 251/56; C07C 253/30
(52) U.S. Cl. ........................................ 564/248
(58) Field of Search ........................... 564/256

(56) References Cited

U.S. PATENT DOCUMENTS
6,441,236 B1 * 8/2002 Grote et al. .............. 564/256

FOREIGN PATENT DOCUMENTS
WO  00/18726  * 4/2000  ......... C07C/249/08

OTHER PUBLICATIONS
Indian Journal of Chem, vol. 30B, Aug. 1991, 749–753, Fadda.

* cited by examiner

*Primary Examiner*—Brian Davis
(74) *Attorney, Agent, or Firm*—Keil & Weinkauf

(57) ABSTRACT

A process for preparing oxime ethers of the formula I,

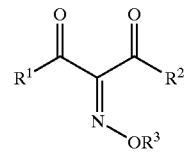

I in which the substituents $R^1$ and $R^2$ can be identical or different and can each be cyano, alkyl, haloalkyl, cycloalkyl, phenyl and naphthyl, and $R^3$ can be alkyl, by alkylation of oximes of the formula II

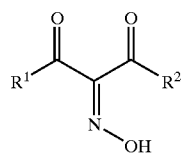

II under basic conditions with an alkylating agent from the group of alkyl halides, dialkyl sulfates and dialkyl carbonates, wherein the reaction is carried out in a mixture consisting of 5 to 25% by weight of polar aprotic solvents selected from the group of nitrites, N-alkylpyrrolidones, cyclic urea derivatives, dimethylformamide and dimethylacetamide, 55 to 95% by weight of nonpolar solvents selected from the group of aliphatic hydrocarbons, aromatic hydrocarbons, alkyl alkylcarboxylates and ethers, and 0 to 25% by weight of water, the contents thereof totaling 100%.

11 Claims, No Drawings

METHOD FOR PRODUCING OXIME ETHERS

This application is a 371 of PCT EP 01/03822 filed Apr. 4, 2001.

The present invention relates to a process for preparing oxime ethers of the formula I

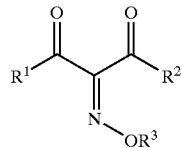

in which the substituents $R^1$ and $R^2$ can be identical or different and can each be cyano, $C_1$–$C_4$-alkyl, $C_1$–$C_4$-halogenalkyl, $C_3$–$C_6$-cycloalkyl, phenyl and naphthyl, and $R^3$ can be $C_1$–$C_4$-alkyl, by alkylation of oximes of the formula II

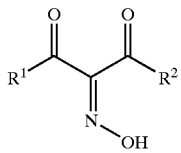

under basic conditions with an alkylating agent from the group of alkyl halides, dialkyl sulfates and dialkyl carbonates, wherein the reaction is carried out in a mixture consisting of
5 to 25% by weight of polar aprotic solvents selected from the group of nitrites, N-alkylpyrrolidones, cyclic urea derivatives, dimethylformamide and dimethylacetamide,
55 to 95% by weight of nonpolar solvents selected from the group of aliphatic hydrocarbons, aromatic hydrocarbons, alkyl alkylcarboxylates and ethers, and
0 to 25% by weight of water, the contents thereof totaling 100%.

Processes for alkylating activated oximes are known from the prior art.

Bull. Acad. Sci. USSR, Div. Chem. Sci. (Engl. Transl.), EN, vol. 28, pp. 121–128 (1979) describes oxime alkylation reactions through diazoalkanes, alkyl halides and dialkyl sulfates; the competition between oxygen and nitrogen alkylation is investigated in particular. Preparation of the O-alkyl ethers of α,α'-biscarbonyloximes in moderate yields in acetone, ethanol, water or diethyl ether is described. To favor O-alkylation it is recommended that the highest possible temperatures be used because the nitrones are thermally unstable, or that the alkylating reagents are as bulky as possible.

Ind. J. Chem., vol 30B, pp. 749–753 (1991) describes the methylation of oximes of the formula II in which $R^1$ and $R^2$ are methyl or phenyl. Reaction with methyl iodide in the presence of anhydrous $K_2CO_3$ in acetone results in the O-methyl ethers in yields of 65 or 67%.

WO-A 00/18726 describes the alkylation of oximes of formula II in various solvents. The reaction can also take place in mixtures of these solvents.

When such syntheses are carried out on an industrial scale there are technical advantages in using water-containing solvent mixtures. A water content does, however, normally lead to losses of yield.

It is an object of the present invention to provide an economic and industrially applicable process for preparing oxime O-alkyl ethers of the formula I which has high selectivity and yields even in water-containing solvent mixtures and is simple to carry out.

We have found that this object is achieved by a process for preparing oxime ethers of the formula I

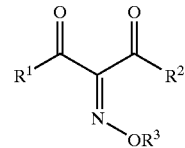

in which the substituents $R^1$ and $R^2$ can be identical or different and can each be cyano, $C_1$–$C_4$-alkyl, $C_1$–$C_4$-haloalkyl, $C_3$–$C_6$-cycloalkyl, phenyl and naphthyl, and $R^3$ can be $C_1$–$C_4$-alkyl, by alkylation of oximes of the formula II

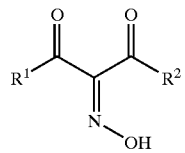

under basic conditions with an alkylating agent from the group of alkyl halides, dialkyl sulfates and dialkyl carbonates, wherein the reaction is carried out in a mixture consisting of
5 to 25% by weight of polar aprotic solvents selected from the group of nitrites, N-alkylpyrrolidones, cyclic urea derivatives, dimethylformamide and dimethylacetamide,
55 to 95% by weight of nonpolar solvents selected from the group of aliphatic hydrocarbons, aromatic hydrocarbons, alkyl alkylcarboxylates and ethers, and
where appropriate up to 25% by weight of water.

In the process of the invention, contrary to the teaching of the prior art, at moderate temperatures surprisingly no nitrone formation is observed, and the O-alkyl ethers are obtained in good to very good yields, despite the use of sterically undemanding alkylating agents and substrates.

Suitable bases are in general salt-like compounds such as alkali metal and alkaline earth metal carbonates such as sodium carbonate, potassium carbonate and magnesium carbonate, and alkali metal bicarbonates such as sodium bicarbonate, also alkali metal acetates such as sodium acetate. Potassium carbonate is particularly preferred.

The base is generally used in the equimolar quantity or in excess; an excess of about 10 to 30% has proven advantageous in many cases. The base can be employed in solid form or as solution, in particular as aqueous solution. For practical reasons, it is preferred to use at least 10% by weight and up to saturated aqueous solutions.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, and N-methylpyrrolidone, N-octylpyrrolidone, cyclic urea derivatives such as dimethylpropyleneurea, dimethyl sulfoxide, dimethylformamide and dimethylacetamide, particularly preferably dimethylformamide and dimethylacetamide, aromatic hydrocarbons such as toluene and ethers such as tert-butyl methyl ether.

The reaction is carried out in a solvent mixture which consists of 5 to 25% by weight, preferably 10 to 20% by weight, of the aforementioned polar aprotic solvents, up to 25% by weight of water and at least 5% by weight, preferably 55 to 95% by weight and particularly preferably 60 to 90% by weight, in particular 60 to 80% by weight, of the aforementioned nonpolar solvents.

It is preferred to carry out the process in water-containing solvent mixtures for technical reasons.

Suitable alkylating agents are alkyl halides, dialkyl sulfates and dialkyl carbonates. Dialkyl sulfates are preferred for economic reasons.

The alkylating agent is generally used in the equimolar quantity or in excess; an excess of about 5 to 15% by weight has proven advantageous in many cases.

For safety reasons, when alkyl halides and dialkyl sulfates are used it is normal to destroy excess alkylating agent after the reaction, and ammonia or amines such as, for example, diethylamine are mostly used for this.

In a preferred embodiment of the process, methylating agents are used.

The reaction is normally carried out at temperatures from 0 to 100° C., preferably at 0 to 50° C. and very particularly preferably at 10 to 25° C. The reaction temperature is normally set appropriate for the thermal stability of the oxime.

The sequence of addition of the reactants is not critical. In a preferred embodiment of the process, the base, as solid or as aqueous solution, is introduced into the solvent, and the oxime and the alkylating agent are added simultaneously and in equimolar quantity to the solvent mixture which contains water where appropriate. In another preferred embodiment, the oxime is added to a part or all of the alkylating agent.

The process of the invention is not restricted to compounds with particular substituents as long as the substituents are inert under the reaction conditions. Aliphatic radicals may be straight-chain or branched. The chain length of the substituents is immaterial for the process of the invention, but for technical reasons radicals with no more than 4 C atoms will normally be chosen.

The process is very particularly preferably used to prepare pentane-2,3,4-trione 3-O-methyloxime.

Alkyl is generally $C_1$–$C_{10}$-alkyl, in particular $C_1$–$C_4$-alkyl, which also applies to haloalkyl; cycloalkyl radicals have three to six ring members.

The substituents $R^1$ and $R^2$ may carry other radicals which are inert under the reaction conditions, the following being mentioned by way of example: halogen, cyano, $SO_3H$, COOH, $COOR^4$, $C_1$–$C_{10}$-alkyl, $C_2$–$C_8$-alkenyl, $C_2$–$C_8$-alkynyl, phenyl or hetaryl; $R^4$ is $C_1$–$C_{10}$-alkyl.

Hetaryl is, for example, furyl, thienyl, pyrrolyl, isoxazolyl, isothiazolyl, pyrazolyl, oxazolyl, imidazolyl, pyridyl, pyridazinyl, pyrimidinyl or triazinyl;

Halogen is chlorine, fluorine, bromine or iodine.

Alkenyl and alkynyl radicals have two to eight, in particular three to six, C atoms.

The oxime O-alkyl ethers obtainable by the process of the invention are suitable as intermediates for preparing dyes or active ingredients in the drugs or crop protection sector.

The following comparative examples illustrate the effect of the features essential to the invention; the examples are intended to explain the process of the invention further:

COMPARATIVE EXAMPLES

1. Methylation in Acetone [Ind. J. Chem., vol. 30B, pp. 749–753 (1991)]

A solution of 12.9 g of pentane-2,3,4-trione 3-oxime in 38.5 ml of acetone and 15.6 g of methyl iodide were added dropwise to a suspension of 16.6 g of potassium carbonate in 40 ml of acetone at about 20° C. with cooling. After stirring at about 20° C. for 2 h, the solvent was distilled off. The residue was dissolved in water and extracted with tert-butyl methyl ether. From the combined organic phases there were obtained 12 g of pentane-2,3,4-trione 3-O-methyloxime (97% pure according to GC analysis), corresponding to a yield of 81.5% of theory.

2. Methylation in Dimethylformamide (DMF)

A solution of 12.9 g of pentane-2,3,4-trione 3-oxime in 38.5 g of DMF and 13.9 g of dimethyl sulfate (DMS) were added dropwise to a suspension of 16.6 g of potassium carbonate in 40 g of DMF at about 20° C. with cooling. After stirring at about 20° C. for 2 h, 2.2 g of diethylamine were added in order to destroy excess DMS and, after stirring at about 20° C. for a further hour, 130 ml of water were added. The solution was extracted with tert-butyl methyl ether. From the combined organic phases there were obtained after washing with 1 N $H_2SO_4$ 12.8 g of pentane-2,3,4-trione 3-O-methyloxime (90% pure according to GC analysis), corresponding to a yield of 80.5% of theory.

3. Methylation in Tert-butyl Methyl Ether (MTBE)

A solution of 12.9 g of pentane-2,3,4-trione 3-oxime in 38.5 g of MTBE and 13.9 g of dimethyl sulfate (DMS) were added dropwise to a suspension of 16.6 g of potassium carbonate in 40 g of MTBE at about 20° C. with cooling. After stirring at about 20° C. for 2 h, 2.2 g of diethylamine were added to destroy excess DMS and, after stirring at about 20° C. for a further hour, 80 ml of water were added. The solution was extracted with tert-butyl methyl ether. From the combined organic phases there were obtained after washing with 1 N $H_2SO_4$ 9.9 g of pentane-2,3,4-trione 3-O-methyloxime (76.7% pure according to GC analysis), corresponding to a yield of 53% of theory.

4. Methylation in Tert-butyl Methyl Ether/Acetone 87:13

A solution of 12.9 g of pentane-2,3,4-trione 3-oxime in 38.5 g of MTBE and 13.9 g of dimethyl sulfate (DMS) were added dropwise to a suspension of 16.6 g of potassium carbonate in a mixture of 30 g of tert-butyl methyl ether (MTBE) and 10 g of acetone at about 20° C. with cooling. After stirring at about 20° C. for 2 h, 2.2 g of diethylamine were added to destroy excess DMS and, after stirring at about 20° C. for a further hour, 80 ml of water were added. The solution was extracted with tert-butyl methyl ether. From the combined organic phases there were obtained after washing with 1 N $H_2SO_4$ 11 g of pentane-2,3,4-trione 3-O-methyloxime (85.8% pure according to GC analysis), corresponding to a yield of 70.0% of theory.

5. Methylation in DMF/MTBE 89:11

A solution of 12.9 g of pentane-2,3,4-trione 3-oxime in 38.5 g of DMF and 13.9 g of dimethyl sulfate (DMS) were added dropwise to a suspension of 16.6 g of potassium carbonate in a mixture of 32 g of dimethyl formamide (DMF) and 8 g of tert-butyl methyl ether (MTBE) at about 20° C. with cooling. After stirring at about 20° C. for 2 h, 2.2 g of diethylamine were added to destroy excess DMS and, after stirring at about 20° C. for a further hour, 130 ml of water were added. The solution was extracted with tert-butyl methyl ether. From the combined organic phases there were obtained after washing with 1 N $H_2SO_4$ 13.5 g of pentane-2,3,4-trione 3-O-methyloxime (91.9% pure according to GC analysis), corresponding to a yield of 86.7% of theory.

6. Methylation in DMF/MTBE 48:52 [WO-A 00/18726]

4.5 kg (32.6 mol) of potassium carbonate were suspended in 3.2 l of methyl tert-butyl ether and one liter of DMF in a 20 l vessel. The mixture was cooled to 0 to −10° C. with stirring. A solution of 4128 g (32 mol) of pentane-2,3,4-trione 3-oxime, 2 l of DMF and 4032 g (32 mol) of diemethyl [sic] sulfate was then metered in over the course of 2 hours at an internal temperature of <25° C. The mixture was then stirred at room temperature for 3.5 hours. 20 l of water was subsequently metered in, the upper organic phase was separated off, the aqueous phase was washed with 2 l of methyl tert-butyl ether, the combined organic phase were washed with 1 l of 5% strength hydrochloric acid, and the solvent was distilled off. 4214 g of the title compound were obtained in a purity of 96.6% (GC percent area) which corresponds to a yield of 89%.

7. Methylation in DMF/MTBE 13:87

A solution of 129.0 g of pentane-2,3,4-trione 3-oxime in 385 g of MTBE and 138.7 g of dimethyl sulfate (DMS) were added dropwise to a suspension of 165 g of potassium carbonate in a mixture of 100 g of dimethylformamide (DMF) and 300 g of tert-butyl methyl ether (MTBE) at about 20° C. with cooling. After stirring at about 20° C. for 2 h, 21.9 g of diethylamine were added to destroy excess DMS and, after stirring at about 20° C. for a further hour, 800 ml of water were added. The solution was extracted with tert-butyl methyl ether. From the combined organic phases there were obtained after washing with 1 N $H_2SO_4$ 144.6 g of pentane-2,3,4-trione 3-O-methyloxime (96.5% pure according to GC analysis), corresponding to a yield of 97.6% of theory.

8. Methylation in DMF/MTBE/Water 13:66:20

A solution of 129 g of pentane-2,3,4-trione 3-oxime in 246 g of MTBE and 132 g of dimethyl sulfate (DMS) were added dropwise to 332 g of a 50% by weight aqueous solution of potassium carbonate, 110 g of dimethylformamide (DMF), 300 g of tert-butyl methyl ether (MTBE) and 7 g of dimethyl sulfate (DMS) at about 17–19° C. with cooling. After stirring at about 20° C. for 2 h, 36.5 g of diethylamine were added to destroy excess DMS and, after stirring at about 20° C. for a further hour, 600 ml of water were added. The solution was extracted with tert-butyl methyl ether. From the combined organic phases there were obtained after washing with 1 N $H_2SO_4$ 136.9 g of pentane-2,3,4-trione 3-O-methyloxime (96.3% pure according to GC analysis), corresponding to a yield of 92.1% of theory.

We claim:

1. A process for preparing oxime ethers of the formula I,

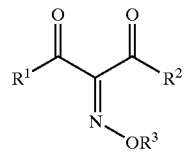

in which the substituents $R^1$ and $R^2$ can be identical or different and can each be cyano, $C_1$–$C_4$-alkyl, $C_1$–$C_4$-haloalkyl, $C_3$–$C_6$-cycloalkyl, phenyl and naphthyl, and $R^3$ can be $C_1$–$C_4$-alkyl,
by alkylation of oximes of the formula II

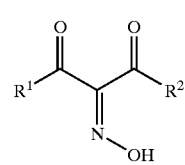

under basic conditions with an alkylating agent from the group of alkyl halides, dialkyl sulfates and dialkyl carbonates,
wherein the reaction is carried out in a mixture consisting of
5 to 25% by weight of polar aprotic solvents selected from the group of nitriles, N-alkyl-pyrrolidones, cyclic urea derivatives, dimethylformamide and dimethylacetamide,
55 to 95% by weight of nonpolar solvents selected from the group of aliphatic hydrocarbons, aromatic hydrocarbons, alkyl alkylcarboxylates and ethers, and
0 to 25% by weight of water,
the contents thereof totaling 100%.

2. A process as claimed in claim 1, where ethers are used as nonpolar solvents.

3. A process as claimed in claim 2, where tert-butyl methyl ether is used.

4. A process as claimed in claim 1, where the reaction is carried out in the presence of water.

5. A process as claimed in claim 1, where dimethylformamide or dimethylacetamide are used as polar solvents.

6. A process as claimed in claim 1, where dialkyl sulfates are used as alkylating agents.

7. A process as claimed in claim 1, where the content of polar solvents is 10 to 25% by weight.

8. A process as claimed in claim 1, where bases selected from the group of bicarbonates, carbonates and acetates are used.

9. A process as claimed in claim 8, where alkali metal or alkaline earth metal carbonates, alkali metal bicarbonates or alkali metal acetates are used.

10. A process as claimed in claim 8, where potassium carbonate is used.

11. A process as claimed in claim 1, where the substituents $R^1$, $R^2$ and $R^3$ in formula I are each $C_1$–$C_4$-alkyl.

* * * * *

UNITED STATES PATENT AND TRADEMARK OFFICE
CERTIFICATE OF CORRECTION

PATENT NO.     : 6,680,410 B2
DATED          : January 20, 2004
INVENTOR(S)    : Goetz et al.

It is certified that error appears in the above-identified patent and that said Letters Patent is hereby corrected as shown below:

<u>Title page,</u>
Item [57], ABSTRACT,
Line 6, after formula II, "nitrites" should be -- nitriles -- .

<u>Column 6,</u>
Line 31, "nitrites" should be -- nitriles -- .

Signed and Sealed this

Twenty-second Day of June, 2004

JON W. DUDAS
*Acting Director of the United States Patent and Trademark Office*